(12) United States Patent
Vergnault et al.

(10) Patent No.: US 9,040,085 B2
(45) Date of Patent: *May 26, 2015

(54) DELAYED RELEASE TABLET WITH DEFINED CORE GEOMETRY

(71) Applicant: Jagotec AG, Muttenz (CH)

(72) Inventors: Guy Vergnault, Kembs (FR); Pascal Grenier, Kappelen (FR); Christophe Dragan, Geispitzen (FR)

(73) Assignee: Jagotec AG, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/329,631

(22) Filed: Jul. 11, 2014

(65) Prior Publication Data

US 2014/0328912 A1 Nov. 6, 2014

Related U.S. Application Data (63) Continuation of application No. 13/713,528, filed on Dec. 13, 2012, which is a continuation of application No. 13/428,548, filed on Mar. 23, 2012, now Pat. No. 8,394,407, which is a continuation of application No. 10/554,538, filed as application No. PCT/IB2004/001693 on Apr. 23, 2004, now Pat. No. 8,168,218.

(30) Foreign Application Priority Data

Apr. 24, 2003 (GB) .................................. 0309342.4

(51) Int. Cl.
*A61K 9/28* (2006.01)
*A61K 9/20* (2006.01)
(Continued)

(52) U.S. Cl.
CPC . *A61K 9/284* (2013.01); *A61K 9/20* (2013.01); *A61K 9/2813* (2013.01); *A61K 9/282* (2013.01); *A61K 31/573* (2013.01); *A61K 9/0002* (2013.01)

(58) Field of Classification Search
CPC ...................................................... A61K 9/20
See application file for complete search history.

(56) References Cited

U.S. PATENT DOCUMENTS 3,870,790 A 3/1975 Lowey et al.
4,867,985 A 9/1989 Heafield et al.
(Continued)

FOREIGN PATENT DOCUMENTS

EP 0463877 A1 1/1992
EP 0673645 A2 9/1995
(Continued)

OTHER PUBLICATIONS

"Exhibit A: Detailed Factual and Legal Basis for Alvogen's Certification that U.S. Patent No. 8,394,407 is Invalid, Unenforceable and/or will not be Infringed by the Manufacture, Use of Sale of Prednisone Delayed-Release Tablets as Defined by Anda No. 204830" of Alvogen Pine Brook, Inc's Providing notice pursuant to Section 505(j)(2)(B)(ii) of the Federal Food, Drug, and Cosmetic Act. Mar. 12, 2013.
(Continued)

*Primary Examiner* — Paul Dickinson
(74) *Attorney, Agent, or Firm* — Mintz Levin Cohn Ferris Glovsky and Popeo, P.C.; Muriel Liberto, Esq.

(57) ABSTRACT

A tablet comprising a core containing an active agent, and a coating, the core being disposed within the coating such that the coating has a thickness about a longitudinal axis (X-Y) of about 4.85 to 4.95 mm. The position of the core within the coating dictating that the active agent is released rapidly after a lag time during which time no active agent is released.

11 Claims, 2 Drawing Sheets

(51) Int. Cl.
A61K 31/573 (2006.01)
A61K 9/00 (2006.01)

(56) References Cited

U.S. PATENT DOCUMENTS

| | | | |
|---|---|---|---|
| 4,871,549 | A | 10/1989 | Ueda et al. |
| 5,279,832 | A | 1/1994 | Greissinger et al. |
| 5,310,558 | A | 5/1994 | Pozzi et al. |
| 5,464,633 | A | 11/1995 | Conte et al. |
| 5,567,696 | A | 10/1996 | McGuire et al. |
| 5,792,476 | A | 8/1998 | Hallgren |
| 6,013,280 | A | 1/2000 | Frisbee et al. |
| 6,183,780 | B1 | 2/2001 | Van Balken et al. |
| 6,245,352 | B1 | 6/2001 | Arbuthnot et al. |
| 6,365,185 | B1 | 4/2002 | Ritschel et al. |
| 6,488,960 | B1 | 12/2002 | Bardsley |
| 6,599,284 | B2 | 7/2003 | Faour |
| 6,620,439 | B1 | 9/2003 | Mehta |
| 6,733,784 | B1 | 5/2004 | Ayres |
| 8,168,218 | B2 | 5/2012 | Vergnault et al. |
| 8,309,124 | B2 | 11/2012 | Vergnault et al. |
| 2004/0018327 | A1 | 1/2004 | Wynn et al. |
| 2005/0008702 | A1 | 1/2005 | Faour et al. |
| 2006/0057200 | A1 | 3/2006 | Schaeffler |
| 2012/0177739 | A1 | 7/2012 | Vergnault et al. |

FOREIGN PATENT DOCUMENTS

| | | |
|---|---|---|
| EP | 0776660 A2 | 6/1997 |
| EP | 1027888 A2 | 8/2000 |
| EP | 0939623 B1 | 2/2002 |
| EP | 1275381 A1 | 1/2003 |
| EP | 1067910 B1 | 5/2004 |
| GB | 874586 A | 8/1961 |
| JP | 2001010950 A | 1/2001 |
| WO | WO-9200064 A1 | 1/1992 |
| WO | WO-9211845 A1 | 7/1992 |
| WO | WO-9319741 A1 | 10/1993 |
| WO | WO-9407470 A1 | 4/1994 |
| WO | WO-9640078 A1 | 12/1996 |
| WO | WO-9901121 A1 | 1/1999 |
| WO | WO-9918938 A1 | 4/1999 |
| WO | WO-0018447 A2 | 4/2000 |
| WO | WO-0108421 A2 | 2/2001 |
| WO | WO-0152819 A1 | 7/2001 |
| WO | WO-0168056 A1 | 9/2001 |
| WO | WO-0180824 A2 | 11/2001 |
| WO | WO-0200204 A1 | 1/2002 |
| WO | WO-02072033 | 9/2002 |
| WO | WO-02072034 A2 | 9/2002 |
| WO | WO-03075919 A1 | 9/2003 |
| WO | WO-03026626 A3 | 10/2003 |
| WO | WO-2004028510 A1 | 4/2004 |
| WO | WO-2004093843 A1 | 11/2004 |
| WO | WO-2004093850 A1 | 11/2004 |
| WO | WO-2004103349 A2 | 12/2004 |
| WO | WO-2005027843 A2 | 3/2005 |

OTHER PUBLICATIONS

Certification Pursuant to L. CIV. R. 11.2 in the case of *Horizon Pharma AG and Jagotec AG* v. *Par Pharmaceutical Companies, Inc. and Par Pharmaceutical, Inc.* (Case 2:33-av-00001) dated Oct. 22, 2013.
Civil Cover Sheet for Complaint filed in the United States District Court for the District of New Jersey in the case of *Horizon Pharma AG and Jagotec AG* v. *Par Pharmaceutical Companies, Inc. and Par Pharmaceutical, Inc.* (Case 2:33-av-00001) on Oct. 22, 2013.
Complaint filed in the United States District Court for the District of New Jersey in the case of *Horizon Pharma AG and Jagotec AG* v. *Par Pharmaceutical Companies, Inc. and Par Pharmaceutical, Inc.* (Case 2:33-av-00001) on Oct. 22, 2013.
Conte et al. "Press-Coated Tablets for Time-Programmed Release of Drugs." *Biomaterials.* 14.13(1993):1017-1023.

Defendant Watson Laboratories, Inc.—Florida's Answer, Separate Defenses, and Counterclaims to Plaintiff's Complaint in the case of *Horizon Pharma AG and Jagotec AG* v. *Watson Laboratories, Inc—Florida.* (Civil Action No. 13-5124 (JEI/JS)) dated Nov. 12, 2013.
Fukui et al. "Studies on Applicability of Press-Coated Tablets Using Hydroxypropylcellulose (HPC) in the Outer Shell for Time-Release Preparation." *J. Control. Release.* 68.2(2000):215-223.
GB Search Report dated Aug. 22, 2003 corresponding to GB 0309342.4.
GB Search Report dated Oct. 23, 2003 corresponding to GB 0309342.4.
*Horizon Pharma AG and Jagotec AG* v. *Watson Laboratories, Inc.—Florida, Actavis Pharma, Inc., Andrix Corporation., and Actavis, Inc.* Complaint for Patent Infringement and Exhibits A-E. Aug. 26, 2013.
International Search Report mailed Oct. 21, 2004 corresponding to PCT/IB2004/001693.
Lin et al. "Compression Forces and Amount of Outer Coating Layer Affecting the Time-Controlled Disintegration of the Compression-Coated Tablets Prepared by Direct Compression With Micronized Ethylcellulose." *J. Pharma. Sci.* 90.12(2001):2005-2009.
Lin et al. "Influence of Excipients, Drugs, and Osmotic Agent in the Inner Core on the Time-Controlled Disintegration of Compression-Coated Ethylcellulose Tablets." *J. Pharma. Sci.* 91.9(2002):2010-2046.
Lin et al. "Micronized Ethylcellulose Used for Designing a Directly Compressed Time-Controlled Disintegration Tablet." *J. Control. Release.* 70(2001):321-328.
Plaintiffs Horizon Pharma AG and Jagotec AG's Answer to Counterclaims of Watson Laboratories, inc—Florida in the case of *Horizon Pharma AG and Jagotec AG* v. *Watson Laboratories, Inc—Florida.* (Civil Action No. 13-5124 (JEI/JS)) dated Dec. 13, 2013.
Report on the Filing or Determination of an Action Regarding a Patent or Trademark in the case of *Horizon Pharma AG* v. *Par Pharmaceutical Companies, Inc.* (Civil Action No. 13-6298 (JEI/JS)) dated Oct. 22, 2013.
Report on the Filing or Determination of an Action Regarding a Patent or Trademark in the case of *Horizon Pharma AG* v. *Watson Laboratories, Inc—Florida.* (Civil Action No. 13-5124 (JEI/JS)) dated Aug. 27, 2013.
Report on the Filing or Determination of an Action Regarding a Patent or Trademark Rule in the case of *Horizon Pharma AG and Jagotec AG* v. *Par Pharmaceutical Companies, Inc. and Par Pharmaceutical, Inc.* (Case 2:33-av-00001) dated Oct. 22, 2013.
Rule 7.1 Disclosure Statement—Horizon Pharma AG in the case of *Horizon Pharma AG and Jagotec AG* v. *Par Pharmaceutical Companies, Inc. and Par Pharmaceutical, Inc.* (Case 2:33-av-00001) dated Oct. 22, 2013.
Rule 7.1 Disclosure Statement—Jagotec AG in the case of *Horizon Pharma AG and Jagotec AG* v. *Par Pharmaceutical Companies, Inc. and Par Pharmaceutical, Inc.* (Case 2:33-av-00001) dated Oct. 22, 2013.
Schmidt et al. "Calcium Phosphates in Pharmaceutical Tableting." *Pharm. World Sci.* 15.3(1993):105-115.
Statement Pursuant to L. CIV R. 10.1 in the case of *Horizon Pharma AG and Jagotec AG* v. *Par Pharmaceutical Companies, Inc. and Par Pharmaceutical, Inc.* (Civil Action No. 13-6298 (JEI/JS)) dated Nov. 11, 2013.
Stipulation of Dismissal in the case of *Horizon Pharma AG and Jagotec AG* v. *Par Pharmaceutical Companies, Inc. and Par Pharmaceutical, Inc.* (Civil Action No. 13-6298 (JEI/JS)) dated Dec. 5, 2013.
Supplemental Information for Patent Cases Involving an Abbreviated New Drug Application (ANDA) in the case of *Horizon Pharma AG and Jagotec AG* v. *Par Pharmaceutical Companies, Inc. and Par Pharmaceutical, Inc.* (Case 2:33-av-00001) dated Oct. 22, 2013.
Watson Laboratories, Inc. "Detailed Factual and Legal Bases for WLF's Paragraph IV Certifications That the Claims of U.S. Patents Nos. 6,488,960; 5,677,329; 8,309,124| 8,168,218, and 8,394,407, Are Imvalid, Unenforceable and/or Not Infringed." Jul. 15, 2013.
Zlatkina. "The Modern Therapeutic Tactics of Inflammatory Bowel Disease, Consilium Medicum." *Gastroenterol.* 6.1(2004):2004 (English Machine Translation Enclosed).

(56) References Cited

OTHER PUBLICATIONS

Certificate of Service of John F. Brenner. Florida in the case of *Horizon Pharma AG and Jagotec AG v. Watson Laboratories, Inc*—Florida. (Civil Action No. 13-5124 (JEI/JS)) dated Sep. 5, 2014.
Certificate of Service of Liza M. Walsh. Florida in the case of *Horizon Pharma AG and Jagotec AG v. Watson Laboratories, Inc*—Florida. (Civil Action No. 13-5124 (JEI/JS)) dated Sep. 5, 2014.
Declaration of Aaron M. Johnson in Support of Defendant Actavis Laboratories FL, Inc.'s Opening Claim of Construction Brief in support of its Proposed Claim Construction for U.S. Patent Nos. 8,309,124 and 8,394,407—Florida in the case of *Horizon Pharma AG and Jagotec AG v. Watson Laboratories, Inc*—Florida. (Civil Action No. 13-5124 (JEI/JS)) dated Jun. 26, 2014.
Declaration of Aaron M. Johnson in Support of Defendant's Responsive Markman Brief. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Declaration of Brenda L. Danek, Ph.D. Florida in the case of *Horizon Pharma AG and Jagotec AG v. Watson Laboratories, Inc*—Florida. (Civil Action No. 13-cv-05124 (JEI/JS)) dated Sep. 5, 2014.
Declaration of Dr. Michael B. Maurin, R.Ph., Ph.D. in Support of Defendant's Opening Claim Construction Biref Regarding U.S. Patent Nos. 8,309,124 and 8,394,407—Florida in the case of *Horizon Pharma AG and Jagotec AG v. Watson Laboratories, Inc*—Florida. (Civil Action No. 13-5124 (JEI/JS)) dated Jun. 26, 2014.
Declaration of Dr. Michael B. Maurin, R.Ph., Ph.D. in Support of Defendant's Responsive Markman Brief. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Defendant Actavis Laboratories FL, Inc.'s Opening Claim Construction Brief—Florida in the case of *Horizon Pharma AG and Jagotec AG v. Watson Laboratories, Inc*—Florida. (Civil Action No. 13-cv-05124 (JEI/JS)) dated Jun. 26, 2014.
Defendant Actavis Laboratories FL., Inc.'s Responsive Markman Brief dated Sep. 5, 2014. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Defendant's Certificate of Service—Florida in the case of *Horizon Pharma AG and Jagotec AG v. Watson Laboratories, Inc*—Florida. (Civil Action No. 13-5124 (JEI/JS)) dated Jun. 26, 2014.
Exhibit 1. Curriculum vita of Michael B. Maurin, R.Ph., Ph.D.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 1. U.S. Patent No. 8,309,124B2 dated Nov. 13, 2012.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 1. U.S. Publication No. US 2007/0287675 published Dec. 13, 2007. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit 2. U.S. Patent No. 8,309,124B2 dated Nov. 13, 2012.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 2. U.S. Patent No. 8,394,407 B2 dated Mar. 12, 2013.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 2. U.S. Patent No. 8,486,423 B2 published on Jul. 16, 2013. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit 3. Declaration of Robert O. Williams III, Ph.D.—Florida in the case of *Horizon Pharma AG and Jagotec AG v. Watson Laboratories, Inc*—Florida. (Civil Action No. 13-cv-05124 (JEI/JS)) dated Jun. 25, 2014.

Exhibit 3. International Patent No. WO 02/072033 A2 published Sep. 19, 2002. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit 3. U.S. Patent No. 8,394,407 B2 dated Mar. 12, 2013.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 4. Amendment and Response to Jul. 17, 2012 Office Action filed in U.S. Appl. No. 13/428,548 on Oct. 16, 2012—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 4. Excerpts from *Remington: The Science and Practice of Pharmacy*. Baltimore, MD: Lippincott Williams & Wilkins. (2000)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 4. *Methocel Cellulose Ethers Technical Handbook*. (2002):1-30. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit 5. Excerpts from *Handbook of Pharmaceutical Excipients*. Rowe et al., eds. London: Pharmaceutical Press. (2003)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 5. The United States Pharmacopeia: The National Formulary. (2000):2253-2254—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 6. Excerpts from *Handbook of Pharmaceutical Excipients*. Wade et al., eds. London: Pharmaceutical Press. (1994)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 6. U.S. Patent No. 6,862,890 dated Mar. 8, 2005.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 7. Excerpts from *Handbook of Pharmaceutical Excipients*. Rowe et al., eds. London: Pharmaceutical Press. (2003)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 7. Excerpts from *Remington: The Science and Practice of Pharmacy*. Baltimore, MD: Lippincott Williams & Wilkins. (1995)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 8. Excerpt from Amicus Court Reporters, Inc. transcript from Jul. 29, 2014. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit 8. Excerpts from *Remington: The Science and Practice of Pharmacy*. Baltimore, MD: Lippincott Williams & Wilkins. (2006)—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit 9. Claims and Amended Claims filed in U.S. Appl. No. 13/428,548. Florida in the case of *Horizon Pharma AG and Jagotec AG v. Watson Laboratories, Inc*—Florida. (Civil Action No. 1:13-cv-05124 (JEI/JS)) submitted Sep. 5, 2014.
Exhibit A. Correspondence from Food and Drug Administration to Timother P. Walbert dated Mar. 12, 2004.—Florida in the case of *Horizon Pharma AG and Jagotec AG v. Watson Laboratories, Inc*—Florida. (Civil Action No. 13-cv-05124 (JEI/JS)) submitted Jun. 26, 2014.
Exhibit A. Oral/Video Deposition of Robert O. Williams III, Ph.D. dated Aug. 21, 2014. Florida in the case of *Horizon Pharma AG and Jagotec AG v. Watson Laboratories, Inc*—Florida. (Civil Action No. 1:13-cv-05124 (JEI/JS)) submitted Sep. 5, 2014.

(56) References Cited

OTHER PUBLICATIONS

Exhibit B. U.S. Patent No. 8,309,124B2 dated Nov. 13, 2012.—Florida in the case of *Horizon Pharma AG and Jagotec AG* v. *Watson Laboratories, Inc*—Florida. (Civil Action No. 13-cv-05124 (JEI/JS)) submitted Jun. 26, 2014.

Exhibit C. U.S. Patent No. 8,394,407 B2 dated Mar. 12, 2013.—Florida in the case of *Horizon Pharma AG and Jagotec AG* v. *Watson Laboratories, Inc*—Florida. (Civil Action No. 13-cv-05124 (JEI/JS)) submitted Jun. 26, 2014.

Exhibit D. U.S. Patent No. 5,792,476 dated Aug. 11, 1998.—Florida in the case of *Horizon Pharma AG and Jagotec AG* v. *Watson Laboratories, Inc*—Florida. (Civil Action No. 13-cv-05124 (JEI/JS)) submitted Jun. 26, 2014.

Exhibit E. U.S. Patent No. 4,867,985 dated Sep. 19, 1989.—Florida in the case of *Horizon Pharma AG and Jagotec AG* v. *Watson Laboratories, Inc*—Florida. (Civil Action No. 13-cv-05124 (JEI/JS)) submitted Jun. 26, 2014.

Exhibit F. U.S. Patent No. 6,183,780 B1 dated Feb. 6, 2001.—Florida in the case of *Horizon Pharma AG and Jagotec AG* v. *Watson Laboratories, Inc*—Florida. (Civil Action No. 13-cv-05124 (JEI/JS)) submitted Jun. 26, 2014.

Opening Claim Construction Brief—Florida in the case of *Horizon Pharma AG and Jagotec AG* v. *Watson Laboratories, Inc*—Florida. (Civil Action No. 13-cv-05124 (JEI/JS)) dated Jun. 26, 2014.

Plantiff's Certificate of Service—Florida in the case of *Horizon Pharma AG and Jagotec AG* v. *Watson Laboratories, Inc*—Florida. (Civil Action 13-cv-5124 (JEI/JS)) dated Jun. 26, 2014.

Plaintiffs Horizon Pharma AG and Jagotec AG's Responsive Claim Constructive Brief. Florida in the case of *Horizon Pharma AG and Jagotec AG* v. *Watson Laboratories, Inc*—Florida. (Civil Action No. 13-cv-05124 (JEI/JS)) dated Sep. 5, 2014.

DELAYED RELEASE TABLET WITH DEFINED CORE GEOMETRY

CROSS REFERENCE TO RELATED APPLICATIONS

The present application claims priority to, and is a Continuation Application of U.S. patent application Ser. No. 13/713,528, filed Dec. 13, 2012, which is a Continuation Application of U.S. patent application Ser. No. 13/428,548 filed Mar. 23, 2012 (now U.S. Pat. No. 8,394,407, issued Mar. 12, 2013, which is a Continuation Application of U.S. patent application Ser. No. 10/554,538 filed Jan. 16, 2007 (now U.S. Pat. Ser. No. 8,168,218, issued May 1, 2012), which is the National Stage of International Application Serial No. PCT/IB2004/001693 filed Apr. 23, 2004, which claims priority to GB 0309342.4, priority date Apr. 24, 2003. Each of the foregoing disclosures are incorporated herein by reference in their entireties.

This invention is concerned with a tablet comprising a core containing a drug substance and a coating that is applied to said core by means of compression-coating techniques. The tablet can contain all manner of drug substances, but is particularly suitable for administering those that are advantageously released only after a predetermined lag time after administration. The tablets are particularly suitable for administering lucocorticosteroids selected from prednisone, prednisolone or methylprednisolone.

Research into the chronopharmacological field has demonstrated the importance of biological rhythms in drug therapy. Very often, optimal clinical outcomes cannot be achieved if a drug is released constantly after ingestion. This is particularly the case if symptoms of a disease display circadian variations. In such cases, drug release should vary in a manner that is sympathetic to these variations in order that drug plasma concentrations are at an optimal therapeutic level only when required to treat symptoms of a disease state.

In particular, if symptoms of a disease become apparent at night, or in the early hours upon waking, the time when a patient must take its medication in order to affect the best clinical outcome requires detailed consideration. For example, most asthma attacks occur in the early hours of the morning, e.g. 4 am to 6 am. This is a result of complex circadian rhythms such as the secretion of hydrocortisone and adrenaline. Ischaemic heart diseases occur most often during the night or in the early waking hours around breakfast time. Stiffness and pain associated with rheumatoid arthritis and osteoarthritis occur in the early waking hours, which is believed to be as a result of the secretion of IL-6 in the early hours of the morning, e.g. around 2 am to 4 am.

With conventional immediate release dosage forms, synchronization of drug administration with a nocturnal circadian rhythm responsible for the symptoms experienced by a patient would require a patient having to be disturbed from sleep to take a medicament during the early hours of the morning in order to achieve the most efficacious clinical outcome. Of course, this would be highly inconvenient for a patient.

Accordingly, there remains a need to provide dosage forms that can be taken at a convenient hour before bedtime that will release an effective dose of a drug substance only after a pre-determined lag time in order to synchronise peak plasma concentrations of drug with a particular circadian rhythm.

Furthermore, particularly in relation to drug substances that have a narrow absorption window, or in the case of drug substances that are adapted to treat a local condition in the colon such as Crohn's disease, ulcerative colitis, IBS and IBD there is also a need to provide a dosage form that rapidly releases the drug substances after reaching the end of the lag time.

Still further, having regard to the varied life styles of patients, in order to reduce the inter- and intra-subject variance in bioavailability there is a need to provide a dosage form that releases a drug with a reliable lag time, and to provide peak plasma drug concentrations at a pre-determined time, irrespective of whether a patient is in a fed or fasted state.

Time controlled release formulations are known in the art that are able to deliver drug substances with a defined release rate after a lag time during which no drug substance is released. Such a dosage form is disclosed in WO 02/072033. This dosage form is characterized by a coating containing a natural or synthetic gum that gels in the presence of aqueous media. The coating acts as a barrier to the ingress of aqueous media into an active-agent-containing core and thereby creating a lag time during which no drug substance is released. The gellable coating acts as a medium through which drug is released in a delayed or modified manner. It is stated that the lag time can be modulated by varying the coating weight.

There are several problems with such an approach: First, release of the drug occurs by means of diffusion through the gelled coating. In the case of drugs that have a narrow absorption window, or in the case of drugs adapted to treat a relatively small affected area of the GI tract or colon, once the lag time has expired it is desirable to release the drug as rapidly as possible to ensure that all or substantially all of the drug released at the desired site. A slow diffusion of the drug is not appropriate in such cases. Further, by attempting to control lag time by controlling the coating weight, the formulator's latitude is limited in this regard, because increasing coating weight adds additional cost to the dosage form, and it also adds to the size of the dosage form, which may make it difficult to swallow for certain patient populations such as minors and for the elderly or infirm. Still further, merely adjusting coat weight does not ensure that a coating is of a desired thickness at a particular site. It remains that if the core is not correctly positioned within a die of a press coating machine, despite having selected a particular coat weight, part of the coating may be unintentionally thinner than desired, resulting in unforeseen premature release of the drug.

The applicant has now surprisingly found that by carefully selecting the geometry of a core within its coating, it is possible to manipulate the coating thickness at specific points on the tablet to ensure an appropriate coating thickness to produce tablets having a specifically tuned lag time. Furthermore, because one is able to increase thickness where it is needed in the coating, one can reduce coating material to allow use of the minimum amount necessary to achieve the desired release characteristics, thus saving on cost of materials and also reducing the overall tablet size.

Still further, the applicant has found that by selecting appropriate core and coating materials, one is able not only to accurately control the lag time, one is also to ensure that all, or substantially all, of the drug substance upon expiry of the lag time is released rapidly and at the absorption site, or the locally affected site.

Figure 1:
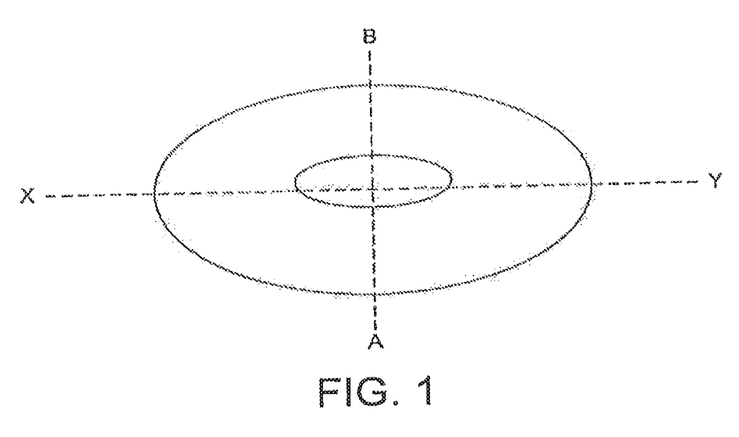
FIG. 1: is a representation of a tablet in cross section showing the coating and core and the axes (A-B) and (X-Y).

Accordingly, in a first aspect of the present invention there is provided a tablet comprising a core containing an drug substance, and a coating around said core, the core being disposed within said coating such that the coating thickness about an axis (X-Y) (see FIG. 1) is thicker than the coating about an axis (A-B) (see FIG. 1) orthogonal to (X-Y), and wherein the thickness of the coating about the axis (X-Y) is selected such that the coating is adapted to rupture upon immersion in an aqueous medium after a period of between about 2 to 6 hours.

According to the present invention, the coating thickness about the axis (X-Y) is thicker than the coating about the axis (A-B). The ratio of the thickness of the coating about the axis (X-Y) to the thickness of the coating about the axis (A-B) may be from 2.2 to 2.6:1.0 to 1.6.

In another aspect of the invention there is provided a tablet comprising a core containing an drug substance and a coating around said core, the core being disposed within said coating such that the coating thickness about an axis (X-Y) is thicker than the coating about an axis (A-B) orthogonal to (X-Y), and the thickness of the coating about the axis (X-Y) is at least about 2.2 mm, particularly about 2.2 to 2.6 mm, more particularly about 2.35 to 2.45 mm.

The thickness of the coating around or about the axis (A-B) is not critical for controlling the lag time. Accordingly, the formulator has some latitude in selecting its thickness. It should not be so thick as to render the final tablet to large, yet on the other hand the coating should not be so thin that the coating is render weak and liable to crack under the slightest mechanical stress. Preferably, the thickness of the coating about the axis (A-B) is about 1.0 to about 1.6 mm. The coating thickness either side of the core on the axis (A-B) may or may not be equal. For example, on a first side of the core (A-core) the coating may have a thickness of about 1.2 to 1.6 mm, more preferably 1.35 to 1.45 mm, whereas on the other side of the core (B-core) the thickness may be about 1.0 to 1.4 mm, more preferably 1.15 to 1.25 mm.

Accordingly, in a particular embodiment of the present invention there is provided a tablet comprising a core containing an drug substance, and a coating, the core being disposed within the coating such that the coating has a thickness about an axis (X-Y) of at least about 2.2 mm, more particularly about 2.2 to about 2.6 mm, still more particularly 2.35 to 2.45 mm, and the thickness of the coating about an axis (A-B) orthogonal to (X-Y) is between 1.0 and 1.6 mm. More particularly, along the axis (A-B) on a first side of the core (A-core) the thickness may be about 12 to 1.6 mm, more preferably 1.35 to 1.45 mm, and on a second side of the core (B-core) the thickness may be about 1.0 to 1.4 mm, more preferably 1.15 to 1.25 mm.

Tablets of the present invention are formed by compression coating methods as will be described in more detail herein below. Compression coated tablets are generally formed by placing a portion of a powdered coating material in a die and tamping the powder into a compact form using a punch. A core is then deposited onto the compacted coating material before the remainder of the coating material is introduced into the die and compression forces are applied to form the coated tablet. To ensure that the core is placed on the tamped coating material to ensure its correct geometry relative to the coating in the final tablet form, it is preferable to employ means for positioning the core in relation to the coating material in a die. Typically such means may be provided by a pin punch. A pin punch is a punch that has a convex surface that contacts the coating material to leave a small depression or hollow in the tamped coating material. Thus, when the core is placed into the die on the tamped material, it sits in the depression or hollow and its correct geometry is assured in the final tablet form.

The thickness of the coating along and about the axis of the direction of movement of the punch (the "(A-B)" axis referred to above) is determined by the amount of coating material added to the die and the compaction force applied to form the tablet. On the other hand, the thickness of the coating along and about the "(X-Y)" axis is determined by the size of the core, its position within the die and the diameter of the die. It will be apparent to the skilled person that there is a plurality of axes (X-Y) orthogonal to the axis of movement of the punch (the "A-B" axis), which extend radially from the centre of the tablet to its circumference, and when the reference is made to the thickness of the coating about an axis X-Y, reference is being made the thickness about any or all of these axes.

During the compression of the coating around the core, the coating material above and below the core (the material along and about the (A-B) axis) is relatively highly compacted and dense. On the other hand, the coating material disposed along and about the (X-Y) axis is subjected to lower compaction forces and is relatively less dense. Accordingly, the material about the (X-Y) axis is relatively porous and permissive towards the ingress of aqueous media. The rate of ingress of the aqueous medium through the coating along the direction of the X-Y axis is, in part, responsible for controlling the release of the drug substance from the core. Once the aqueous medium contacts the core, the core reacts by swelling or effervescing thereby to break open the core generally along the direction of ingress of the aqueous media (i.e. the X-Y axis) to form to essentially two hemispheres of coating material that may remain conjoined, which has an appearance of an opened clam shell. The reaction of the core material to the presence of the aqueous medium is likewise in part responsible for controlling the release of drug substance from the core.

The hardness of the tablet is preferably at least 60 Newtons, e.g. 60 to 80 Newtons, and more particularly 60 to 75 Newtons. Hardness may be measured according to a process described in The European Pharmacopoeia 4, 2.9.8 at page 201. The test employs apparatus consisting of 2 opposing jaws, one of which moves towards the other. The flat surfaces of the jaws are perpendicular to the direction of movement. The crushing surfaces of the jaws are flat and larger than the zone of contact with the tablet. The apparatus is calibrated using a system with a precision of one Newton. The tablet is placed between the jaws. For each measurement, the tablet is oriented in the same way with respect to the direction of the applied force. Measurements are carried out on 10 tablets. Results are expressed in terms of the mean, minimum and maximum values (in Newtons) of the force needed to crush the tablets.

Tablets having a hardness within this range are mechanically robust to withstand forces generated in the stomach, particularly in the presence of food. Furthermore, the tablets are sufficiently porous about the (X-Y) plane of the tablet to permit ingress of physiological media to the core at an appropriate rate to ensure that the drug substance is released within an appropriate lag time, e.g. within 2 to 6 hours.

As stated above, it is a preferred aspect of the present invention that the tablets are adapted to release a drug substance from the core after a pre-determined lag time, as well as being adapted to release all, or substantially all, of the drug substance within a very short period of time after the expiry of the lag time. This ensures that all, or substantially all, of the drug is released at the intended absorption site along the GI tract, or onto the affected site of the GI tract if the condition to be treated is a local topical condition. It is preferred that the tablets of the present invention release all, or substantially all of a drug substance within about ½ hour to about 1 hour after the selected lag time.

This aspect of the present invention is important for delivering drugs having a rather narrow absorption window in the upper GI tract, such as the glucocorticosteroids referred to above. In such cases, the drug should be released before the tablet can pass into the bowel, where absorption of such drugs is poor. It is made particularly important if the tablet is intended to perform in the same manner independent of the effects of food. It is well known that the rate at which a tablet will pass through the GI tract will vary depending on whether a patient is in a fed or fasted state. In the fasted state, a tablet will typically clear the stomach within about ½ hour and 1 hour after ingestion, and thereafter take a further 4 to 5 hours to clear the upper GI tract through the ileosecal junction. In a fed state, a tablet may take as long as 4 hours to be cleared from the stomach, and a further 4 to 5 hours to clear the upper GI tract. Accordingly, if a tablet is to release of all, or substantially all, of its drug into the upper GI tract irrespective of the fed state of a patient, it is preferable that the release the drug after the lag time occurs within a time limit referred to in the paragraph above.

It should be understood that whereas it is desirable that no drug substance is released during the lag time, some release may occur. However, any release of drug substance during the lag time should not exceed 10% of the total amount of drug substance in the core.

The coating employed in a tablet according to the present invention is preferably formed of insoluble or poorly water soluble hydrophobic material. In use, the coating optimally acts merely as a barrier to the ingress of aqueous physiological media thereby providing a drug release lag time. For the reasons set forth above, optimally the tablet should have the minimum thickness possible consistent with the desired lag time. Accordingly, employing water insoluble or poorly, soluble hydrophobic coating materials, one is able to produce a coating that is relative recalcitrant to the ingress of moisture and so long lag times can be achieved with relatively thin coatings.

Further, in order to achieve the rapid release of drug substance after the lag time has expired, it is desirable that the coating contains no, or substantially no, ingredients that swell and gel agents to such an extent that the coating acts as a diffusion barrier to the release of drug substance. In this regard, it is preferable that the coating contains no, or substantially no, materials such as natural or synthetic gums that modulate release of the drug substance through an intact swollen coating. Drug substance is released from the core as a result of the physical rupturing of the coating and not as a result of the drug substance diffusing through a swollen coating material. That the mechanism of drug release is substantially dependent on the physical splitting of the coating, and not on a diffusion process through a swellable and gellable coating, means that a wide range of drug substances can be delivered from tablets according to the invention in a reliable and reproducible manner.

The tablet coating may contain one or more water insoluble or poorly soluble hydrophobic excipients. Such excipients may be selected from any of the known hydrophobic cellulosic derivatives and polymers including alkylcellulose, ethylcellulose, hydroxypropyl cellulose, hydroxypropylmethyl cellulose, carboxymethyl cellulose, and derivatives thereof; polymethacrylic polymers, polyvinyl acetate and cellulose acetate polymers; fatty acids or their esters or salts; long chain fatty alcohols; polyoxyethylene alkyl ethers; polyoxyethylene stearates; sugar esters; lauroyl macrogol-32 glyceryl, stearoyl macrogol-32 glyceryl, and the like. Hydroxypropylmethyl cellulose materials are preferably selected from those low Mw and low viscosity materials such as E-Type methocel, and 29-10 types as defined in the USP.

Other agents or excipients that provide hydrophobic quality to coatings may be selected from any waxy substance known for use as tablet excipients. Preferably they have a HLB value of less than 5, and more preferably about 2. Suitable hydrophobic agents include waxy substances such as carnauba wax, paraffin, microcrystalline wax, beeswax, cetyl ester wax and the like; or non-fatty hydrophobic substances such as calcium phosphate salts, e.g. dibasic calcium phosphate.

Preferably the coating contains a calcium phosphate salt, glyceryl behenate, and polyvinyl pyrollidone, or mixtures thereof, and one or more adjuvants, diluents, lubricants or fillers.

Preferred components in the coating are as follows, with generally suitable percentage amounts expressed as percentage weight of the coating.

Polyvinyl pyrollidone (Povidone) is preferably present in amounts of about 1 to 25% by weight or the coating, more particularly 4 to 12%, e.g. 6 to 8%.

Glyceryl behenate is an ester of glycerol and behenic acid (a C22 fatty acid). Glyceryl behenate may be present as its mono-, di-, or tri-ester form, or a mixture thereof. Preferably it has an HLB value of less than 5, more preferably approximately 2. It may be present in amounts of about 5 to 85% by weight of the coating, more particularly from 10 to 70% by weight, and in certain preferred embodiments from 30 to 50%.

Calcium phosphate salt may be the dibasic calcium phosphate dihydrate and may be present in an amount of about 10 to 90% by weight of the coating, preferably 20 to 80%, e.g. 40 to 75%.

The coating may contain other common tablet excipients such as lubricants, colourants, binders, diluents, glidants and taste-masking agents or flavourants.

Examples of excipients include colourants such a ferric oxide, e.g. yellow ferric oxide; lubricants such as magnesium stearate; and glidants such as silicon dioxide, e.g. colloidal silicon dioxide. Yellow ferric oxide may be used in amounts of about 0.01 to 0.5% by weight based on the coating; magnesium stearate may be present in amounts of 1 to 20% by weight of the coating, more preferably 2 to 10%, e.g. 0.5 to 1.0%; and colloidal silica may be used in amounts of 0.1 to 20% by weight of the coating, preferably 1 to 10%, more preferably 0.25 to 1.0%.

The core comprises in addition to a drug substance, a disintegrating agent or mixtures of disintegrating agents used in immediate release formulations and well know to persons skilled in the art. The disintegrating agents useful in the exercise of the present invention may be materials that effervesce and or swell in the presence of aqueous media thereby to provide a force necessary to mechanically disrupt the coating material.

Preferably a core contains, in addition to the drug substance, cross-linked polyvinyl pyrollidone and croscarmellose sodium.

The following is a list of preferred core materials. The amounts are expressed in terms of percentage by weight based on the weight of the core.

Cross-linked polyvinyl pyrollidone is described above and is useful as a disintegrating agent, and may be employed in the core in the amounts disclosed in relation to the core.

Croscarmellose sodium is an internally cross-linked sodium carboxymethyl cellulose (also known as Ac-Di-Sol) useful as a disintegrating agent.

Disintegrating agents may be used in amounts of 5 to 30% by weight based on the core. However, higher amounts of certain disintegrants can swell to form matrices that may modulate the release of the drug substance. Accordingly, particularly when rapid release is required after the lag time it is preferred that the disintegrants is employed in amounts of up to 10% by weight, e.g. about 5 to 10% by weight.

The core may additionally comprise common tablet excipients such as those described above in relation to the coating material. Suitable excipients include lubricants, diluents and fillers, including but not limited to lactose (for example the monohydrate), ferric oxide, magnesium stearates and colloidal silica.

Lactose monohydrate is a disaccharide consisting of one glucose and one galactose moiety. It may act as a filler or diluent in the tablets of the present invention. It may be present in a range of about 10 to 90%, preferably from 20 to 80%, and certain preferred embodiments from 65 to 70%.

As stated above, it is an important aspect of the present invention that core is correctly located within the coating to ensure that a tablet has the appropriate coating thickness. In this way, lag times will be reliable and reproducible, and intra-subject and inter-subject variance in bioavailability can be avoided. It is advantageous to have a robust in process control to ensure that tablets in a batch contain cores having the appropriate geometry in relation to the coating. Controls can be laborious in that they require an operator to remove random samples from a batch and to cut them open to physically inspect the quality of the core (i.e. whether it is intact, and whether it is correctly located). Furthermore, if a significant number of tablets from the sample fail, a complete batch of tablets may be wasted. Applicant has found that if one adds to the core a strong colourant such as iron oxide, such that the core visibly contrasts with the coating when as strong light is shone on the tablet, it is possible for any faults in the position or integrity of the core to be picked up automatically by a camera appropriately located adjacent a tabletting machine to inspect tablets as they are ejected therefrom. In this way, if a faulty tablet is identified it is possible to halt production and correct any problems in the manufacturing process quickly, thereby potentially avoiding wastage of batch quantities of tablets.

Whereas colourants contained in the core are useful for this purpose, equivalent solutions are also possible. For example, instead of a colourant, one can include a material that is opaque to x-rays, such as barium sulphate. If an x-ray imager is then coupled to a tablet machine, the core will contrast with the coating material and the x-ray imager will pick up any faults in the positioning or integrity of the core in a similar fashion.

The amount of drug substance employed in tablets of the present invention will depend on the particular drug substance used, the condition of the patient and the nature and severity of the condition to be treated. A typical drug loading might be from 1 to 50% by weight of the core.

As stated above a wide variety of drug substances may be employed in the present invention. Drugs for treating conditions the symptoms of which result from nocturnal circadian rhythms are particularly suitable. Accordingly, drugs for treating incontinence, sleep disorders, apnoea, asthma, epilepsy, bronchitis, parkinsonism, rheumatoid arthritis, allergic rhinitis and ischaemic heart diseases, cluster and migraine headache, congestive heart failure, and depression are particularly suitable for use in tablets according to the present invention. Further, drug substances that are metabolized by cytochrome P450 are also particularly suitable, they include:—

Amitriptyline, caffeine, clomipramine, clozapine, fluvoxamine, haloperidol, imipramine, mexilitine, oestradiol, olanzapine, paracetamol, propranolol, tacrine, theophylline, warfarin, Bupropion, Cyclophosphamide, Celecoxib, Diclofenac, Flubiprofen, Ibuprofen, glimepirideindome, thacin, naproxen, phenyloin, piroxicam, tenoxicam, citalopram, diazepam, lansoprazole, omeprazole, pantoprozole, propanolol, topiramate, Alpranolol, chlorpromazine, clomipramine, codeine, Desipramine, dextromethorphan, diphenhydramine, donepezil, flecainide, fluoxetine, labetalol, Methadone, metoprolol, mianserin, nortripyline, ondansetron, oxprenolol, oxycodone, paroxetine, perhehexylene, pethidine, promethazine, risperdone, thioridazine, ticlopidine, timolol, trimipramine, venlafaxine, paracetamol, alprazolam, amiodarone, budesonide, buprenorphine, buspirone, Calcium Channel Blockers, carbamazepine, cisapride, clarithromycin, clonazepam, cocaine, cortisol, cyclosporine, dexamethasone, erythromycin, fentanyl, ketoconazole, losartan, miconazole, midazolam, quinidine, sertraline, statins, tacrolimus, tamoxifen, TCAs, triamzolam, zolpidem, or mixtures thereof.

Additional examples of drug classes and drugs that can be employed in tablets of the present invention include:

antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride and triprolidine hydrochloride);

antibiotics (e.g., penicillin V potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate HCL, lincomycin HCL, novobiocin sodium, nitrofurantoin sodium, metronidazole hydrochloride); antituberculosis agents (e.g., isoniazid);

cholinergic agents (e.g., ambenonium chloride, bethanecol chloride, neostigmine bromide, pyridostigmine bromide);

antimuscarinics (e.g., anisotropine methylbromide, clidinium bromide, dicyclomine hydrochloride, glycopyrrolate, hexocyclium methylsulfate, homatropine methylbromide, hyoscyamine sulfate, methantheline bromide, hyoscine hydrobromide, oxyphenonium bromide, propantheline bromide, tridihexethyl chloride);

sympathomimetics (e.g., bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate);

sympatholytic agents (e.g., phenoxybenzamine hydrochloride); miscellaneous autonomic drugs (e.g., nicotine);

iron preparations (e.g., ferrous gluconate, ferrous sulphate);

haemostatics (e.g., aminocaproic acid);

cardiac drugs (e.g., acebutolol hydrochloride, disopyramide phosphate, flecainide acetate, procainamide hydrochloride, propranolol hydrochloride, quinidine gluconate, timolol maleate, tocainide hydrochloride, verapamil hydrochloride);

antihypertensive agents (e.g., captopril, clonidine hydrochloride, hydralazine hydrochloride, mecamylamine hydrochloride, metoprolol tartrate); vasodilators (e.g., papaverine hydrochloride);

non-steroidal anti-inflammatory agents (e.g., choline salicylate, ibuprofen, ketoprofen, magnesium salicylate, meclofenamate sodium, naproxen sodium, tolmetin sodium);

opiate agonists (e.g., codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, propoxyphene hydrochloride);

anticonvulsants (e.g., phenobarbital sodium, phenyloin sodium, troxidone, ethosuximide, valproate sodium);

tranquilizers (e.g., acetophenazine maleate, chlorpromazine hydrochloride, fluphenazine hydrochloride, prochlorperazine edisylate, promethazine hydrochloride, thioridazine hydrochloride, trifluoroperazine hydrochloride, lithium citrate, molindone hydrochloride, thiothixine hydrochloride);

chemotherapeutic agents (e.g., doxorubicin, cisplatin, floxuridine, methotrexate, combinations thereof);

lipid lowering agents (e.g., gemfibrozil, clofibrate, HMG-CoA reductase inhibitors, such as for example, atorvastatin, cerivastatin, fluvastatin, lovastatin, pravastatin, simvastatin);

$H.sub.2$-antagonists (e.g., cimetidine, famotidine, nizatidine, ranitidine HCl);

anti-coagulant and anti-platelet agents (e.g., warfarin, cipyridamole, ticlopidine);

bronchodilators (e.g., albuterol, isoproterenol, metaproterenol, terbutaline);

stimulants (e.g., benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate);

barbiturates (e.g., amylobarbital sodium, butabarbital sodium, secobarbital sodium);

sedatives (e.g., hydroxyzine hydrochloride, methprylon); expectorants (e.g., potassium iodide);

antiemetics (e.g., benzaquinamide hydrochloride, metoclopropamide hydrochloride, trimethobenzamide hydrochloride);

gastro-intestinal drugs (e.g., ranitidine hydrochloride); heavy metal antagonists (e.g., penicillamine, penicillamine hydrochloride);

antithyroid agents (e.g., methimazole);

genitourinary smooth muscle relaxants (e.g., flavoxate hydrochloride, oxybutynin hydrochloride);

vitamins (e.g., thiamine hydrochloride, ascorbic acid);

unclassified agents (e.g., amantadine hydrochloride, colchicine, etidronate disodium, leucovorin calcium, methylene blue, potassium chloride, pralidoxime chloride.

steroids, particularly glucocorticoids (e.g., prednisolone, methylprednisolone, prednisone, cortisone, hydrocortisone, methylprednisolone, betamethasone, dexamethasone, triamcinolone).

Notwithstanding the general applicability of the tablets in relation to a wide range of drug substances, the present invention is particularly suited to delivery of the glucocorticosteroids aforementioned, and particularly prednisone, prednisolone and methylprednisolone. These steroids are useful in the treatment i.a, of rheumatoid arthritis and joint pain. As already stated, the symptoms of these conditions appear according to a circadian rhythm and with great predictability during the early hours of the morning. Accordingly, the glucocorticosteroids, and in particular prednisone are eminently suited for delivery from tablets according to this invention not only because of their narrow absorption window, but also because a tablet may be administered in the evening before bedtime anytime around 8 pm until midnight, e.g. around 10-12 at night, to deliver maximum plasma concentration of the drug substance before maximum secretion of IL-6 (which occur around 2 am to 4 am), thereby effectively addressing the underlying causes of the morning symptoms. In this way, these symptoms are more effectively treated.

As used above, prednisone refers to the compound and its salts or derivatives thereof, including prednisone 21 acetate.

As used above, prednisolone refers to the compound and its salts or derivatives including the 21-acetate, its 21-tert-butyl acetate, 21-succinate sodium salt, 21-stearoylglycolate, 21-m-sulphobenzoate sodium salt, and its trimethylacetate.

Methylprednisolone, as used above refers to the compound or and its salts and derivatives thereof including its 21 acetate, 21-phosphate disodium salt, 21-succinate sodium salt, and its acetonate.

Typically a core may contain about 0.1 to 50% by weight, more particularly 1 to 20%, still more particularly 1 to 10% by weight of steroid based on the total weight of the core. In the case of prednisone, it may be employed in amounts to provide a total weight per unit dosage form of 1 or 5 mg, to offer convenience and flexibility of dosing, although dosage forms containing larger or smaller amounts of drug substance could be employed if desired.

Particularly preferred tablets according to the invention comprising in the core a glucocorticosteroid selected from the group consisting of prednisone, prednisolone and methylprednisolone, and cross-linked polyvinyl pyrollidone, cross-linked sodium carboxymethyl cellulose, and one or more adjuvants diluents, lubricants or filler materials as hereinabove described. Preferably the coating comprises a calcium phosphate salt, glyceryl behenate, cross-linked polyvinyl pyrollidone and one or more adjuvants, diluents, lubricants or filler materials as hereinabove described.

The composition of one particularly preferred embodiment of the invention is:

Core of 5 Mg Prednisone Tablet:
Prednisone 8.33%
Lactose monohydrate 64.47%
Povidone 6.67%
Croscarmellose sodium 18.33%
Red ferric oxide 0.5%
Magnesium stearate Vegetable origin 1.0%
Colloidal silicon dioxide 0.5%
Coating
Dibasic calcium phosphate dihydrate 50%
Glyceryl behenate 40%
Povidone 8.40%
Yellow ferric oxide 0.1%
Magnesium stearate Vegetable origin 1.0%
Colloidal silicon dioxide 0.5%
Another preferred embodiment is as follows;
Core of 1 mg prednisone tablet:
Prednisone 1.67%
Lactose monohydrate 71.13%
Povidone 6.67%
Croscarmellose sodium 18.33%
Red ferric oxide 0.5%
Magnesium stearate Vegetable origin 1.0%
Colloidal silicon dioxide 0.5%
Coating
Dibasic calcium phosphate dihydrate 50%
Glyceryl behenate 40%
Povidone 8.40%
Yellow ferric oxide 0.1%
Magnesium stearate Vegetable origin 1.0%
Colloidal silicon dioxide 0.5%

It is surprising that the tablets containing the glucocorticosteroids display such rapid release given that the rate of release relies to some extent on the wetting of the core, and these steroids are rather hydrophobic in nature.

The tablets described above are press-coated tablets comprising a core and a coating covering said core. However, variants of this basic construction are within the ambit of the present invention. Thus, the press-coating may be further coated with an outer coating that may be functional and/or aesthetic in its design. For example, functional coatings may include the addition an immediate release coating containing a drug substances that may be the same or different to the drug substance contained in the core.

In this mariner, the tablet can affect a pulsatile release that is of use in treating symptoms based on circadian rhythms, such as sleep disorders. In this regard one can employ sedative hypnotics in such dosage forms, for example those drug substances mentioned described in U.S. Pat. No. 6,485,746. Pulsatile release dosage forms may also find general applicability with a wide range of active substances for the treatment of a wide range of indications to provide patients with a more convenient dosage schedule. For example, pulsatile release cart provide an alternative to multiple administrations of immediate release forms.

Functional coatings also include enteric coatings covering the press-coating. Enteric coated forms may be of use in treating local conditions in the bowel such as Crohn's disease, ulcerative colitis, IBS and IBD. In this embodiment, the enteric coating would prevent release of any drug before the tablet enters the bowel.

Aesthetic coatings include taste, masking coatings and coloured coatings as a generally well known in the art.

It is well known in the art that food can change the bioavailability of a drug. Food can alter the bioavailability of a drug by various means such as delaying gastric emptying, changes in gastrointestinal pH, changes in luminal metabolism, and physical and chemical reactions of food items with a dosage form or drug substance. This change in bioavailability as a consequence of food intake is often referred to as a "food effect". Food effects are quite common in modified-release dosage forms, and also for drugs that have either poor solubility or poor permeability or both (BCS Class II, III and IV).

The applicant has surprisingly found that a tablet that is adapted to release, all, or substantially all, of a drug contained therein within a time ($T_{lag}$) of between 2 and 6 hours (median time) after administration.

Furthermore, the applicant has surprisingly developed a tablet adapted to release a drug substance after a lag time that can deliver a drug to a patient, which upon absorption the peak drug concentration $C_{max}$ will be reached in a time $T_{max}$ that is independent of a patient's food intake.

$T_{max}$ is a term well known in the art that refers to the time elapsed between drug administration and the maximum plasma concentration $C_{max}$ is reached. $C_{max}$ is also an art recognized term that relates to the peak plasma concentration of a drug.

$T_{max}$ is an important parameter particularly in relation to medicaments that are intended to be taken at a time convenient for a patient, but which release drug substances after a lag time in order to synchronise drug release with a circadian rhythm, and in particular a nocturnal circadian rhythm. By way of example, the glucocorticosteroids, referred to above, e.g. prednisone, are useful in the treatment of i.a. arthritic conditions such as rheumatoid arthritis and osteoarthritis. Debilitating symptoms are often experienced by a patient upon waking. Current therapy requires a patient to take Decortin$^R$ upon waking. However, this is not the most efficacious way of treating the symptoms, as they are believed to be associated with the secretion of IL-6, which occurs during the early morning hours, e.g. from about 2 to 4 am. A medicament that can reach C that is coincident with or anticipates the release of IL-6 is potentially of greater benefit to a patient. Furthermore, given the varied lifestyles of individuals, patients taking medicament between 8 pm and bedtime, e.g. from 10 pm to midnight, may be in a variety of fed states, it is even more advantageous that $T_{max}$ should be independent of food intake.

Medicaments that can have a pre-determined lag time, and which release drug substance after this lag time in a manner that provides a $T_{max}$ independent of considerations of the fed or fasted state of a patient are of potentially great benefit, not only in relation to the glucocorticosteroids and the treatment of arthritis, but for other active substances that are advantageously delivered in synchronicity with a circadian rhythm, or even in relation to drug substances whose efficacy depends on their ability to be delivered accurately to a particular absorption site, or a locally diseased site along the GI tract and bowel. Such medicaments are provided by the present invention.

Currently, there are no bioavailability or bioequivalence regulatory guidelines available for $T_{max}$. However, the Guidance For Industry "Food Effect Bioavailability and Fed Bioequivalence Studies", US Department of Health (CDER) Dec. 2002 suggests that any difference in $T_{max}$ should not be clinically relevant. Whether such a difference will be clinically relevant will depend on the drug delivered and the particular indication. Applicant has found that in respect of formulations of the present invention the effect of food on the median value of $T_{max}$ is a difference of only about +/-20%, more particularly +/-10%

Still further, applicant has found medicaments containing drug substances exhibiting no significant effect of food with respect to bioavailability of the drug substance in terms of $C_{max}$ and AUC.

The "food effect" as it relates to the bioavailability of drug substances is a well documented phenomenon in relation to drug delivery that describes the variance in uptake of a drug substance by patients depending upon whether the patients are in fed or fasted states. The presence or absence of a food effect may be quantified by making Area under the Curve (AUC) and/or $C_{max}$ measurements according to methods well known in the art. Typically AUC measurements and $C_{max}$ measurements are made by taking timed biological fluid samples and plotting the serum concentration of drug substance against time. The values obtained represent a number of values taken from subjects across a patient population and are therefore expressed as mean values expressed over the entire patient population. By comparing the mean AUC and/or $C_{max}$ values, one can determine whether a drug substance experiences a food effect.

Food effect studies may be conveniently carried out on an adequate number of healthy volunteers, the number being sufficient to generate sufficient data for appropriate statistical assessment to be made. Preferably the number of subjects should not be less than 12.

To study the effect of food on the bioavailability of a drug substance one may use any conventional study design known in the art, for example a randomised; balanced single-dos; two-treatment, two-period, two-sequence crossover design. Analysis may be carried out using any of the programs known in the art such as SAS PROC GLM, software from the SAS institute, Cary N.C.

In quantitative terms, a drug substance may be said to exhibit no food effect if a 90% confidence interval (CI) for the ratio of means (population geometric means based on log transformed data) of fed and fasted treatments fall within the interval of 0.8 to 1.25 for AUC and/or 0.7 to 1.43 for $C_{max}$.

Accordingly, the present invention provides in another of its aspects a tablet as defined herein above displaying a ratio AUG fed/fasted after single dosing of 0.8 to 1.25 or the ratio $C_{max}$ fed/fasted after single dosing of 0.7 to 1.43.

A "fed" subject conveniently may be considered as a subject that has fasted for at least 10 hours before receiving a standard FDA recognised high fat meal. The medicament may then be administered with water shortly after completion of the meal, e.g. within 5 minutes thereof. Preferably no food should be taken for a period of, e.g. 4 hours after receiving medicament although small quantities of water may be permitted after, e.g. 2 hours after receiving the medicament.

A "fasted" subject conveniently may receive medicament with water after at least 10 hours fasting. Thereafter, no food may be taken for a period of, e.g. 4 hours although small quantities of water may be taken after, e.g. 2 hours after receiving medicament.

A standard FDA high fat meal as referred to hereinabove may comprise any meal that would be expected to provide maximal perturbation due to the presence of food in the GI tract. Said high fat meal typically may comprise 50% of its caloric value in fat. A representative example may be 2 eggs fried in butter, 2 strips of bacon, 2 slices toast with butter, 4 ounces fried potato, and 8 ounces milk.

By application of the teachings of the present invention tablets may be provided that display reduced variability in resumption/bioavailability levels achieved both for individual patients receiving a drug as well as between individuals.

The tablets of the present invention may be packaged in a variety of ways. Generally an article for distribution includes a container for holding the tablets. Suitable containers are well known to persons skilled in the art and include materials such as bottles, foil packs and the like. In addition, the container will have a label and an insert that describes the contents of the container and any appropriate warnings or instructions for use. It is an advantage of the present invention that the insert and/or label may contain instructions that the tablet may be taken with or without food, or may be absent a warning or instruction that the tablet should be taken only with food or only without food.

The invention provides in another aspect, a method of forming tablets as herein above described. The tablets may be formed on conventional press coating equipment. Typically such equipment is composed of a series of die are arranged on a rotating platform. The die are removably mounted in the platform such that differently sized die may be employed as appropriate. Each die is hollow to receive a lower punch. The punch is positioned within the die such that the upper surface of the punch and the inner surface of the die define a volume for receiving a precise amount coating material. Once loaded, the platform is rotated until the die is positioned under an upper punch. The upper punch is then urged down onto the coating material under a defined compression force and the coating material is pre-compressed or tamped between the upper and lower punch. A pre-formed core is then fed into die to rest on the tamped coating. Conventional press coating apparatus may be equipped with centering devices that enable cores to be positioned both vertically and radially. This might be achieved by a tamping process, whereby an initial amount of coating material is placed in a die and is tamped with a shaped punch, such as a pin punch, that leaves an indentation in the coating material in which to receive a core. Thereafter, in a second filling operation, a precise amount of coating material is fed into the die to cover the core, and an upper punch compresses the coating material with a defined compaction force to form tablets according to the present invention.

The compression force applied during the tamping process is relatively light and is just sufficient to provide a bed of coating material to receive the core and to prevent movement of the coating material as a result of centrifugal force. Subsequent compression to form the tablet may be adjusted to give tablets of requisite hardness. Preferably, this compression force is 400 kg, although this may be adjusted by +/− 30% in order to give tablets of the required hardness.

The amount of coating material fed into the die can be precisely defined having regard to the density of the coating material to ensure after compression that the tablet is formed with the required coating thickness about the (A-B) axis; and the dimensions of the die is selected to provide the thickness about the X-Y axis. Should it be necessary to change the thickness of the coating, die of appropriate internal dimensions may be placed in the rotating platform, and the amount of coating material fed into the die may be adjusted accordingly.

Suitable rotary tablet machines having high process speeds are known in the art and need no further discussion here.

Cores may likewise be formed using a conventional rotary tablet machine. Cores are preferably compressed under compression forces sufficient to provide cores having a hardness of about 60 Newtons at least, e.g. 50 to 70 Newtons. Cores having hardness in this range give desired release characteristics. If desired, the cores can be formed at the same time as the press coated tablets are produced. In such case, one might employ a Manesty Dry Cota. Such a press consists of two side-by-side and inter-connected presses where the core is made on one press before being mechanically transferred to the other press for compression coating. Such equipment and techniques for making tablets using such equipment are known in the art and no more needs to be said about this here.

Cores are preferably formed according to wet granulation techniques generally known in the art. In a typical procedure, core materials are sieved and blended. Granulating fluid, typically water is then added to the blend and the mixture is homogenized to form a granulate, which is then sprayed dried or dried on a fluid bed drier to obtain a granulate with requisite residual moisture. Preferably the residual moisture content is from about 0.4 to 2.0% by weight. The granulate is then sized by passing it through screens of desired aperture. At this stage, any adjuvants are sized and added to the granulate to form, the core composition suitable for compression. The skilled person will appreciate that a coating composition can be formed in an analogous manner. The skilled person will also appreciate that granulates may be obtained having a range of particle sizes. It is preferred that the coating granulate has a fine fraction that is less than 30%. By "fine fraction" is meant granulate having particle size of up to about 63 microns.

Preferred features for the second and subsequent aspects of the invention may be as for the first aspect mutatis mutandis.

There now follows a series of examples that serve to illustrate the invention.

EXAMPLE 1

Preparation of a Prednisone-containing Tablet

The active core was prepared for the press coated system as follows. The composition of the core is detailed in Table 1. Lactose monohydrate (Lactose Pulvis•$H_2O$®, Danone, France and Lactose Fast Flo® NF 316, Foremost Ing. Group, USA) is a filling agent with interesting technical and functional properties. Lactose Pulvis•$H_2O$ is used in a blend prepared by wet granulation and Lactose Fast Flo is used in a blend prepared for direct compression. Microcrystalline cellulose (Avicel® pH 101, FMC International, Ireland) is used as an insoluble diluent for direct compression. Polyvinyl pyrrolidone (Plasdone® K29-32, ISP Technology, USA) is a granulating agent, soluble in water, which has the ability of binding the powder particles. Croscarmellose sodium (Ac- Di-Sol®, FMC Corporation, USA) is used in the formulation as a super disintegrant. As the external phase, magnesium stearate (Merck, Switzerland) was added as a lubricant and silicon dioxide (Aerosil® 200, Degussa AG, Germany) in order to improve flow properties of the granular powder.

TABLE 1

| Ingredients | Content (mg/tablet) |
|---|---|
| Prednisone | 5.00 |
| Lactose (Lactose Pulvis H$_2$O NF 316) | 39.10 |
| Polyvinyl pyrrolidone (Plasdone ® K29-32) | 4.00 |
| Sodium carboxymethyl cellulose (Ac-Di-Sol ®) | 11.00 |
| Magnesium stearate | 0.60 |
| Silicon dioxide (Aerosil ® 200) | 0.30 |
| Total | 60.00 |

The coating of the prednisone press coated tablet is of a hydrophobic, water insoluble nature. This barrier is mainly composed of dibasic calcium phosphate (Emcompress®, Mendell, USA) and glyceryl behenate (Compritol® 888ATO, Gattefossé, Prance). Polyvinylpyrrolidone (Plasdone® K29-32) is a granulating agent, soluble in water, which has the ability of binding the powder particles. Yellow ferric oxide (Sicovit® Yellow 10, BASF, Germany) was added as a dye. A detailed composition of this barrier blend is given in table 2.

TABLE 2

| Composition of the coating | |
|---|---|
| Ingredients | Content (%) |
| Dibasic calcium phosphate (Emcompress ®) | 50.00 |
| Glyceryl Behenate (Compritol ® 888 ATO) | 40.00 |
| Polyvinylpyrrolidone (Plasdone ® K29-32) | 8.40 |
| Yellow Ferric Oxide (Sicovit ® yellow 10 E 172) | 0.10 |
| Silicon dioxide (Aerosil ® 200) | 0.50 |
| Magnesium stearate | 1.00 |
| Total | 100.00 |

The required amounts of prednisone, Ac-Di-Sol®, Lactose Pulvis H$_2$O®, Plasdone® K29-32 were weighed and manually sieved with a screen having 0.710 mm apertures. The components were homogeneously mixed in a Niro-Fielder PMA 25-litre mixing granulator for 6 min at impeller speed 250 rpm without chopper. A prednisone assay was performed on this premix. Subsequently, the granulating solution (purified water, 25.47% of the weight of the dry blend) was added within 4 min at impeller speed 250 rpm and chopper speed 1500 rpm, using a nozzle H1/4VV-95015 (spraying rate of 250 g/min). Mixing was continued for homogenisation and massing of the wet mass for 3 min at impeller speed 500 rpm and chopper speed 3000 rpm.

The mixed wet granulate was then dried in a Glatt WSG5 fluidised air bed drier. The inlet temperature was maintained at 45° C. during drying. The drying lasted 20 min to get a granulate with a residual moisture less than 2.5%. The yielded dry granulate was calibrated in a Frewitt MGI 205 granulator using a screen with 0.8 nm apertures for 3 min at speed 244 osc/min (graduation 7). Appropriate amounts of Aerosil® 200 and magnesium stearate were manually sieved using a screen, with 1.0 mm apertures. Half of the dry granulate was put in a Niro-Fielder PMA 25-litre mixing granulator, followed by Aerosil® 200 and then by the other half of the dry granulate. The ingredients were mixed for 2 min at impeller speed 250 rpm. Finally, magnesium stearate was added and mixing was continued for 2 min at impeller speed 250 rpm.

The coating blend was prepared according to the process described below. Batch size for the barrier blend was 13 kg. Weighed amounts of Emcompress®, Compritol® 888 ATO, Lactose pulvis•H$_2$O®, Plasdone® K29-32 and Sicovit® Yellow 10 E 172 were manually sieved with a screen having 0.710 mm apertures. They were placed in a Niro-Fielder PMA 65-litre mixing granulator. Then, the components were homogeneously mixed for 6 min, at impeller speed 200 rpm, without chopper. Subsequently, the granulating solution (purified water, 8.12% of the weight of the dry blend) was added within 2 min at impeller speed 200 rpm and chopper speed 1500 rpm using a nozzle 4,9 (spraying rate of 520 g/min). Mixing was continued for homogenisation and massing for 1 min at impeller speed 400 rpm and chopper speed 3000 rpm.

The mixed wet granulate was then dried in a Niro-Fielder TSG 2 fluidised air bed dryer. The inlet temperature was maintained at 45° C. during drying. The drying lasted 33 min to have residual moisture less than 2.5%. The yielded dry granulate was calibrated in a Frewitt MGI 205 granulator using a screen having 0.8 mm apertures for 4 min at speed 214 osc/min (graduation 7). Appropriate amounts of Aerosil® 200 and magnesium stearate were manually sieved using a screen with 1.0 min apertures.

Half of the dry granulate was put in a Niro-Fielder PMA 65-litre, followed by Aerosil® 200 and then by the other half of the dry granulate. The ingredients were mixed for 2 min at impeller speed 200 rpm, without chopper. Finally, magnesium stearate was added and mixing was continued for 2 more minutes at impeller speed 200 rpm, without chopper.

440 rug of coating blend was press coated on a core to provide press coated tablets (9 mm diameter). 305 mg of coating blend was press coated on a core to provide press coated tablets (8 mm diameter). These different press coatings were done utilising a Kilian RIM tabletting machine. First and second loading hoppers are filled up with the coating granulate. Between the two loading hoppers, the machine is equipped with a transfer system adapted to feed the cores. For each tablet, the first loading hopper supplies with about half of the quantity to be applied to the core. Then, the feeding system provides and positions a core centred in the die. Subsequently, the second loading hopper supplies with the other half of the quantity to be applied to the core. The compression step then occurs.

TABLE 3

| Equipment implemented for the manufacturing process | | |
|---|---|---|
| Equipment | Brand name/Type | Manufacturer/Supplier |
| Mixing granulator | Niro-Fielder PMA 25/65 litres | Aéromatic-Fielder AG, Bubendorf, Switzerland |
| Fluidised air bed dryer | Glatt WSG5 | Maschinen und apparatebau AG, Pratteln, Switzerland |
| Fluidised air bed dryer | Niro-Fielder TSG 2 | Aéromatic-Fielder AG, Bubendorf, Switzerland |
| Granulator | Frewitt MGI 205 | Frewitt SA, Granges-Pacot, Switzerland |
| Infrared moisture analyser | Mettler PE 360 Moisture Analyzer | Mettler Toledo AG, Greifensee, Switzerland |
| Multilayer tablet press | Hata HT-AP55LS-U/3L | Elisabeth-Carbide, Antwerp, Belgium |
| Dry coating tablet press | Kilian RUD | Kilian & Co GmbH, Cologne, Germany |

EXAMPLE 2

(In Vitro Dissolution Profile)

The in vitro dissolution profile of a tablet containing a 5 mg loading of prednisone prepared according to the method of Example 1 was determined using USP dissolution apparatus No. 2 (paddles) and stationary baskets and applying a stirring rate of 100 rpm. The dissolution medium was purified water, with a volume of 500 ml.

Figure 2:
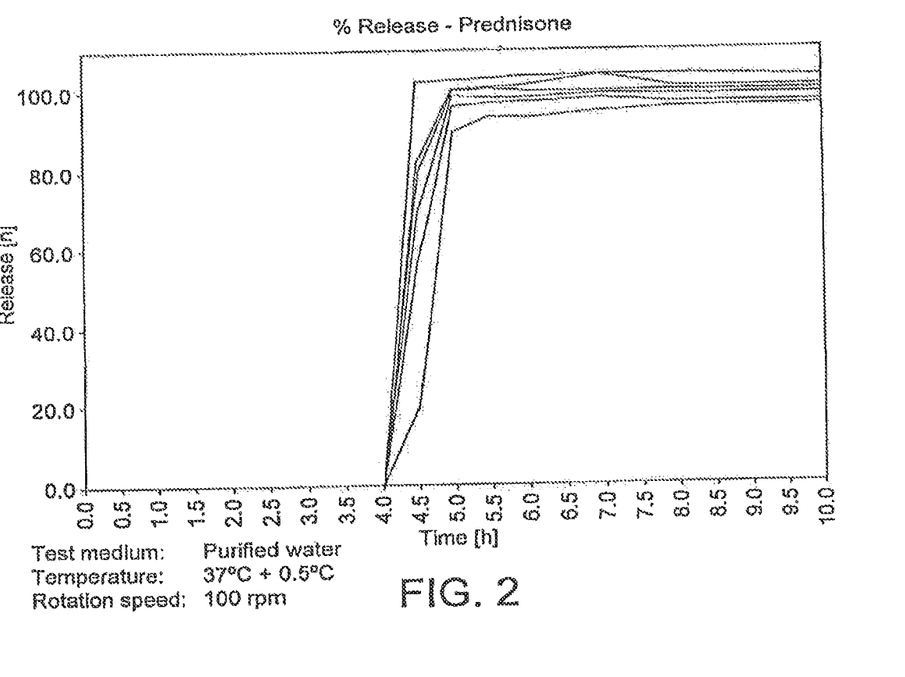
FIG. 2: Shows an in-vitro dissolution profile of the dosage form of Example 2.

After 4 hours no drug substance release is observed. However, within 4.5 hours there is approximately 80% release and by 5 hours 100% release of the drug substance (see FIG. 2).

EXAMPLE 3

A study was carried out to determine the effect of food on the bioavailability of a 5 mg prednisone tablet described above.

The study did not compare the tablet in the fed and fasted state. Rather, the study was adjusted to take into account the chrono-pharmacokinetics of prednisone and the fact that it is to be administered in the evening, e.g. about 8 pm, which is required in order that the blood plasma levels will peak before secretion of IL-6 to improve the efficacy of the treatment. Thus the study was designed to compare the tablet during real time administration and with likely food intake scenarios at this time. It was considered unreasonable that at 8 pm a subject would be approximately 8 hours fasted. Accordingly, the following food intake scenarios were tested:

a) To simulate a fasted state at 8 pm in the evening, a light meal was given 2½ hours before administration that contained a limited number of calories (i.e. 22% of total daily calories and with a limited fat content of 15.5 g) and being devoid of any slowly digestible nutrients. This is called the "semi-fasted" state.

The composition of this meal consisted of brown bread, margarine, cheese spread, an apple (skin removed) and fruit cocktail in syrup.

b) Fed state is simulated by giving a higher fat meal ½ hour before dosing containing 35% of the daily intake of calories and 26 g of fat.

An assumption made was that in the case of the semi-fasted state, after 2½ hours the stomach was already emptied, or substantially emptied of food, The composition of the high fat meal was pasta with spaghetti sauce, soup and vegetables, Apple juice, Ice cream and whipped cream.

The methodology consisted of an open, randomized, 3-period crossover single oral dose study with 7 days washout periods. The patient population consisted of 27 healthy male volunteers.

The pharmacokinetics of the formulation was compared for each of the fed and semi-fasted states with a standard immediate release form (Decortin$^R$) administered at 2 am.

In the semi-fasted state the formulation exhibited a median lag time of 3.5 hours. Relative to Decortin$^R$ dosed at 2 am, the formulation was fully bioequivalent with a $C_{max}$ of 97% and relative bioavailability of 101% ($AUC_{0-infinity}$).

In the fed state, the median lag time was 4 hours. $C_{max}$ was 105% compared to Decortin$^R$, and relative bioavailability ($AUC_{0-infinity}$) was 113%.

Compared to the formulation in the semi-fasted state, the formulation in the fed state was 108% on $C_{max}$ and 112% on $AUC_{0-infinity}$.

These results demonstrate that formulations of the present invention display excellent bioavailability with no significant effect of food.

What is claimed is:

1. A method of administering a glucocorticosteroid active substance selected from prednisone, prednisolone, and methylprednisolone to a patient in need thereof comprising
administering to the patient an oral dosage form comprising a defined core and a compression coating completely covering the core,
wherein the core comprises the glucocorticosteroid active substance and further comprises at least one disintegrating agent that, upon exposure to aqueous media, provides a force to rupture the coating,
wherein the compression coating comprises at least one excipient selected from
fatty acids or their esters or salts;
long chain fatty alcohols;
polyoxyethylene alkyl ethers;
polyoxyethylene stearates;
sugar esters;
lauroyl macrogol-32 glyceryl; and
stearoyl macrogol-32 glyceryl,
wherein the compression coating lacks ingredients that swell and gel to such an extent that the compression coating acts as a diffusion barrier to the release of the active substance, and further provided that the compression coating contains substantially no natural synthetic gum, and
wherein the oral dosage form has an in vitro dissolution profile, as determined using purified water, with a volume of 500 mL in a USP dissolution apparatus No. 2 (paddles) with stationary baskets and a stirring rate of 100 rpm, such that after 4 hours, no active substance is released from the oral dosage form; and by 5 hours, 100% of the active substance is released from the oral dosage form.

2. The method according to claim 1, wherein the compression coating further comprises at least one excipient selected from cellulosic derivatives and polymers and polymethacrylic polymers.

3. The method according to claim 1, wherein the compression coating further comprises alkylcellulose.

4. The method according to claim 1, wherein the dosage form comprises 1 mg prednisone.

5. The method according to claim 1, wherein the dosage form comprises 5 mg prednisone.

6. A method of administering a glucocorticosteroid active substance selected from prednisone, prednisolone, and methylprednisolone to a patient in need thereof comprising
administering to the patient an oral dosage form comprising a defined core and a compression coating completely covering the core,
wherein the core comprises the glucocorticosteroid active substance substance and further comprises at least one disintegrating agent that, upon exposure to aqueous media, provides a force to rupture the coating,
wherein the compression coating comprises at least one excipient selected from
fatty acids or their esters or salts;
long chain fatty alcohols;
polyoxyethylene alkyl ethers;
polyoxyethylene stearates;
sugar esters;
lauroyl macrogol-32 glyceryl; and
stearoyl macrogol-32 glyceryl,
wherein the compression coating lacks ingredients that swell and gel to such an extent that the compression coating acts as a diffusion barrier to the release of the active substance, and further provided that the compression coating contains substantially no natural or synthetic gum, and
wherein the compression coating ruptures upon immersion in an aqueous medium after a period of time between about 2 to about 6 hours to release the glucocorticosteroid active substance.

7. The method according to claim 6, wherein the dosage form comprises 1 mg prednisone.

8. The method according to claim 6, wherein the dosage form comprises 5 mg prednisone.

9. A method of administering a glucocorticosteroid active substance selected from prednisone, prednisolone, and methylprednisolone to a patient in need thereof comprising
   administering to the patient an oral dosage form comprising a defined core and a compression coating completely covering the core,
   wherein the core comprises the glucocorticosteroid active substance substance and further comprises at least one disintegrating agent that, upon exposure to aqueous media, provides a force to rupture the coating,
   wherein the compression coating comprises at least one excipient selected from
      fatty acids or their esters or salts;
      long chain fatty alcohols;
      polyoxyethylene alkyl ethers;
      polyoxyethylene stearates;
      sugar esters;
      lauroyl macrogol-32 glyceryl; and
      stearoyl macrogol-32 glyceryl,
   wherein the compression coating lacks ingredients that swell and gel to such an extent that the compression coating acts as a diffusion barrier to the release of the active substance, and further provided that the compression coating contains substantially no natural or synthetic gum, and
   wherein the oral dosage form releases not more than 10% of the active substance prior to expiry of a lag time; the oral dosage form releases substantially all of the active substance within about 1 hour after the expiry of the lag time; and the lag time is a time between 2 to 6 hours after administration of the oral dosage form to the patient.

10. The method according to claim 9, wherein the dosage form comprises 1 mg prednisone.

11. The method according to claim 9, wherein the dosage form comprises 5 mg prednisone.

* * * * *